(12) United States Patent
Fikfak et al.

(10) Patent No.: US 10,653,510 B2
(45) Date of Patent: May 19, 2020

(54) STENT INCLUDING DISPLACEMENT CAPABILITIES

(71) Applicant: BOSTON SCIENTIFIC SCIMED, INC., Maple Grove, MN (US)

(72) Inventors: Vid Fikfak, Houston, TX (US); Marc Garbey, Houston, TX (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 94 days.

(21) Appl. No.: 15/807,527

(22) Filed: Nov. 8, 2017

(65) Prior Publication Data

US 2018/0125633 A1 May 10, 2018

Related U.S. Application Data

(60) Provisional application No. 62/419,800, filed on Nov. 9, 2016.

(51) Int. Cl.
*A61F 2/04* (2013.01)
*A61F 2/852* (2013.01)
(Continued)

(52) U.S. Cl.
CPC ............ *A61F 2/04* (2013.01); *A61F 2/852* (2013.01); *A61F 2/91* (2013.01); *A61F 2/07* (2013.01);
(Continued)

(58) Field of Classification Search
CPC ........ A61F 2/04; A61F 2/90; A61F 2002/041; A61F 2002/044; A61F 2002/045;
(Continued)

(56) References Cited

U.S. PATENT DOCUMENTS

| 5,064,435 A | 11/1991 | Porter |
| 5,103,817 A * | 4/1992 | Reisdorf ........... A61M 16/0436 128/207.14 |

(Continued)

FOREIGN PATENT DOCUMENTS

| EP | 2085050 A1 | 8/2009 |
| EP | 2386275 A1 | 11/2011 |

(Continued)

OTHER PUBLICATIONS

International Search Report, International Application No. PCT/US2017/060725, dated Feb. 6, 2018 (4 pgs).

*Primary Examiner* — Paul B Prebilic
(74) *Attorney, Agent, or Firm* — Seager, Tufte & Wickhem, LLP

(57) ABSTRACT

An example medical device for treating a body lumen is disclosed. The medical device includes an expandable scaffold positionable within a body lumen wherein the body lumen has an inner surface. The medical device also includes a support member extending circumferentially around and attached to an outer surface of the expandable scaffold. The support member is configured to be positioned between the outer surface of the expandable scaffold and the inner surface of the body lumen and at least a portion of the support member is configured to shift relative to the inner surface of the body lumen. Further, shifting the support member shifts the scaffold longitudinally from a first position within the body lumen to a second position within the body lumen with the scaffold in an expanded state to accommodate peristalsis.

20 Claims, 14 Drawing Sheets

(51) Int. Cl.
*A61F 2/91* (2013.01)
*A61F 2/07* (2013.01)

(52) U.S. Cl.
CPC . *A61F 2002/044* (2013.01); *A61F 2210/0014* (2013.01); *A61F 2220/0008* (2013.01); *A61F 2220/0058* (2013.01); *A61F 2220/0075* (2013.01); *A61F 2230/0065* (2013.01); *A61F 2230/0069* (2013.01); *A61F 2250/0008* (2013.01); *A61F 2250/0039* (2013.01); *A61F 2250/0063* (2013.01); *A61F 2250/0098* (2013.01)

(58) Field of Classification Search
CPC .. A61F 2/852; A61F 2/2409; A61F 2002/075; A61F 2250/0039; A61F 2220/0025; A61F 2250/0063; A61F 2250/006; A61F 2250/001; A61F 2250/0003; A61F 2220/0008; A61F 2250/0065
See application file for complete search history.

(56) References Cited

U.S. PATENT DOCUMENTS

| | | | |
|---|---|---|---|
| 5,397,355 A | 3/1995 | Marin et al. | |
| 5,425,739 A | 6/1995 | Jessen | |
| 5,522,881 A | 6/1996 | Lentz | |
| 5,669,930 A | 9/1997 | Igarashi | |
| 5,876,448 A | 3/1999 | Thompson et al. | |
| 5,937,861 A * | 8/1999 | Augustine | A61M 16/04 128/207.14 |
| 6,007,575 A | 12/1999 | Samuels | |
| 6,187,034 B1 | 2/2001 | Frantzen | |
| 6,395,019 B2 | 5/2002 | Chobotov | |
| 6,695,878 B2 | 2/2004 | McGuckin, Jr. et al. | |
| 6,729,356 B1 | 5/2004 | Baker et al. | |
| 6,926,724 B1 | 8/2005 | Chu | |
| 7,108,715 B2 | 9/2006 | Lawrence-Brown et al. | |
| 7,125,464 B2 | 10/2006 | Chobotov et al. | |
| 7,150,758 B2 | 12/2006 | Kari et al. | |
| 7,235,099 B1 | 6/2007 | Duncavage et al. | |
| 7,628,804 B2 * | 12/2009 | Flagle | A61F 2/07 623/1.24 |
| 7,740,791 B2 | 6/2010 | Kleine et al. | |
| 7,806,857 B2 | 10/2010 | Khosravi et al. | |
| 8,226,708 B1 | 7/2012 | Murch | |
| 8,465,538 B2 | 6/2013 | DiMatteo et al. | |
| 8,512,414 B2 | 8/2013 | Musani | |
| 8,591,570 B2 | 11/2013 | Revuelta et al. | |
| 8,652,204 B2 | 2/2014 | Quill et al. | |
| 8,753,407 B2 | 6/2014 | Nguyen | |
| 8,834,558 B2 | 9/2014 | Nissl | |
| 8,979,892 B2 | 3/2015 | Shalev | |
| 8,986,368 B2 | 3/2015 | Gill et al. | |
| 9,005,275 B2 | 4/2015 | Cassivi et al. | |
| 9,138,336 B2 | 9/2015 | Carman et al. | |
| 9,179,921 B1 | 11/2015 | Morris | |
| 10,064,626 B2 * | 9/2018 | Celermajer | A61B 17/12109 |
| 2001/0010012 A1 * | 7/2001 | Edwin | A61F 2/07 623/1.13 |
| 2005/0090888 A1 | 4/2005 | Hines et al. | |
| 2007/0255394 A1 * | 11/2007 | Ryan | A61F 2/2412 623/1.24 |
| 2010/0063579 A1 | 3/2010 | An | |
| 2010/0256754 A1 * | 10/2010 | Styrc | A61F 2/2412 623/2.18 |
| 2010/0298631 A1 * | 11/2010 | Stack | A61F 2/04 600/37 |
| 2011/0190905 A1 | 8/2011 | Behan | |
| 2011/0182461 A1 | 11/2011 | Shin et al. | |
| 2012/0046684 A1 * | 2/2012 | Evans | A61F 2/07 606/194 |
| 2013/0150950 A1 | 6/2013 | Schlick et al. | |
| 2014/0243965 A1 | 8/2014 | Benson et al. | |
| 2014/0343683 A1 | 11/2014 | Jeon et al. | |
| 2015/0045881 A1 * | 2/2015 | Lim | A61F 2/2418 623/2.38 |
| 2015/0119974 A1 | 4/2015 | Rothstein | |
| 2015/0320578 A1 | 11/2015 | Bui et al. | |
| 2016/0058585 A1 | 3/2016 | Seddon et al. | |
| 2016/0120638 A1 | 5/2016 | Michalak | |

FOREIGN PATENT DOCUMENTS

| | | |
|---|---|---|
| EP | 2803338 A1 | 11/2014 |
| KR | 20000056338 A | 9/2000 |

* cited by examiner

STENT INCLUDING DISPLACEMENT CAPABILITIES

CROSS-REFERENCE TO RELATED APPLICATIONS

This application claims priority under 35 U.S.C. § 119 to U.S. Provisional Application Ser. No. 62/419,800, filed Nov. 9, 2016, the entirety of which is incorporated herein by reference.

TECHNICAL FIELD

The present disclosure pertains to medical devices, and methods for manufacturing medical devices. More particularly, the present disclosure pertains to examples of expandable stents having axial displacement capabilities to accommodate peristaltic motion and methods for manufacturing and using such devices.

BACKGROUND

Implantable medical devices (e.g., expandable stents) may be designed to provide a fluid pathway for digested material, blood, or other fluid to flow therethrough following a medical procedure. Some medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances, it may be desirable to design stents to radially reinforce a body lumen at a treatment site while also allowing the body lumen to maintain its functional properties. However, some stents that are designed to include sufficient radial strength to open a body lumen may also tend to migrate along the body lumen due to peristalsis (i.e., the involuntary constriction and relaxation of the muscles of the esophagus, intestine, and colon which push the contents of the canal therethrough). One method to reduce stent migration may include utilizing a support structure in combination with the stent device. For example, in some instances it may be desirable to use a support structure to position the stent within the body lumen (e.g., adjacent to a target site) whereby the support structure allows the stent a degree of maneuverability within the body lumen (e.g., whereby the support structure allows the stent to axially displace along the body lumen to accommodate peristaltic motion).

Therefore, in some instances it may be desirable to design a stent which utilizes a support structure in combination with the stent device. Examples of medical devices including a support structure are disclosed herein.

BRIEF SUMMARY

This disclosure provides design, material, manufacturing method, and use alternatives for medical devices. An example medical device for treating a body lumen includes an expandable scaffold positionable within a body lumen wherein the body lumen has an inner surface. The medical device also includes a support member extending circumferentially around and attached to an outer surface of the expandable scaffold. The support member is configured to be positioned between the outer surface of the expandable scaffold and the inner surface of the body lumen and at least a portion of the support member is configured to shift relative to the inner surface of the body lumen. Further, shifting the support member shifts the scaffold longitudinally from a first position within the body lumen to a second position within the body lumen with the scaffold in an expanded state to accommodate peristalsis.

Alternatively or additionally to any of the embodiments above, wherein the scaffold includes a first end region and a second end region opposite the first end region, wherein the support member is positioned between the first end region and the second end region.

Alternatively or additionally to any of the embodiments above, wherein the first end region, the second end region or both the first and second end regions include a flared portion.

Alternatively or additionally to any of the embodiments above, wherein the support member is configured to radially deform.

Alternatively or additionally to any of the embodiments above, wherein the expandable scaffold, the support member or both the expandable scaffold and the support member include a covering.

Alternatively or additionally to any of the embodiments above, wherein the covering provides a pathway for material to flow therethrough.

Alternatively or additionally to any of the embodiments above, wherein the support member comprises a plurality of filaments woven together to form a torus surrounding the scaffold.

Alternatively or additionally to any of the embodiments above, wherein the torus includes a centrally located aperture, and wherein the scaffold extends through the centrally located aperture.

Alternatively or additionally to any of the embodiments above, wherein the plurality of filaments are woven to the scaffold.

Alternatively or additionally to any of the embodiments above, wherein the plurality of filaments are welded to the scaffold.

Alternatively or additionally to any of the embodiments above, wherein the torus is configured to roll along the inner surface of the body lumen while remaining attached to the scaffold.

Alternatively or additionally to any of the embodiments above, wherein the support member further includes an anchoring member and one or more support arms attached to and extending from the outer surface of the scaffold to the anchoring member.

Alternatively or additionally to any of the embodiments above, wherein the plurality of support arms spaced around the outer surface of the expandable scaffold.

Alternatively or additionally to any of the embodiments above, wherein the one or more support arms are each attached to the outer surface of the scaffold at an attachment point, and wherein the one or more support arms are configured to pivot about the attachment point as the scaffold shifts from the first position within the body lumen to the second position within the body lumen.

Another example medical device includes:

an expandable stent positionable within a body lumen, the body lumen having an inner surface; and an expandable support member attached to the stent, the support member including a centrally located aperture;

wherein the stent is configured to extend through the aperture of the support member;

wherein the support member is configured to space the stent away from the inner surface of the body lumen;

wherein at least a portion of the support member is configured to shift relative to the inner surface of the body lumen, and wherein shifting the support member shifts the stent longitudinally from a first position within the body lumen to a second position within the body lumen with the stent in an expanded state to accommodate peristalsis.

Alternatively or additionally to any of the embodiments above, wherein the stent includes a first end region and a second end region, and wherein first end region, the second end region or both the first and second end regions include a flared portion.

Alternatively or additionally to any of the embodiments above, wherein the support member is configured to radially deform.

Alternatively or additionally to any of the embodiments above, wherein the stent, the support member or both the stent and the support member include a covering configured to provide a pathway for material to flow therethrough.

Alternatively or additionally to any of the embodiments above, wherein the support member comprises a plurality of filaments woven together to form a torus surrounding the stent.

An example method of treating the esophagus includes:
  advancing a medical device to a target site within the esophagus, the medical device including:
    an expandable scaffold; and
    a support member extending circumferentially around and attached to an outer surface of the expandable scaffold;
  radially expanding the scaffold and the support member to an expanded state such that the support member is positioned between an inner surface of the esophagus and an outer surface of the stent in the expanded state; and
  shifting at least a portion of the support member in the expanded state relative to the inner surface of the esophagus, wherein shifting the support member shifts the scaffold longitudinally from a first position within the esophagus to a second position to accommodate peristalsis in the esophagus.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

DETAILED DESCRIPTION

Figure 1:
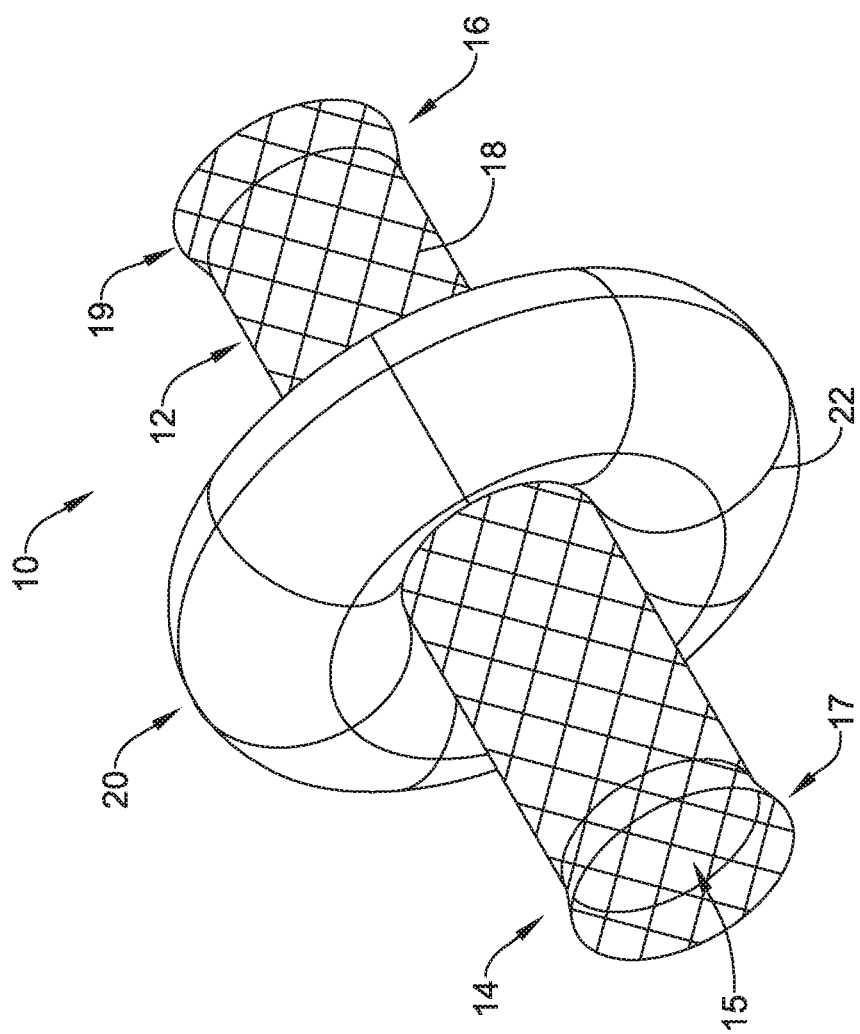
FIG. 1 illustrates an example stent including a support structure.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, medical devices (e.g., expandable stents) may be designed provide a fluid pathway for digested material, blood, or other fluid to flow therethrough following a medical procedure. Some medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances, it may be desirable to design stents to radially reinforce a body lumen at a treatment site while also allowing the body lumen to maintain its functional properties. However, some stents that are designed to include sufficient radial strength to open a body lumen may also tend to migrate along the body lumen due to peristalsis (i.e., the involuntary constriction and relaxation of the muscles of the esophagus, intestine, and colon which push the contents of the canal therethrough). One method to reduce stent migration may include utilizing a support structure in combination with the stent device. For example, in some instances it may be desirable to use a support structure to position the stent within the body lumen (e.g., adjacent a target site) whereby the support structure allows the stent a degree of maneuverability within the body lumen (e.g., whereby the support structure allows the stent to axially displace along the body lumen) after implantation in the body lumen. Therefore, in some instances it may be desirable to design a stent which utilizes a moveable support structure in combination with the stent device.

FIG. 1 illustrates an example implantable medical device 10. Implantable medical device 10 may be any of a number of devices that may be introduced endoscopically, subcutaneously, percutaneously or surgically to be positioned within an organ, tissue, or lumen, such as an esophagus, intestine, colon, urethra, trachea, bronchus, bile duct, blood vessel, or the like. Medical device 10 may be configured to be positioned in a body lumen for a variety of medical applications. For example, medical device 10 may be used to provide a pathway for food or other digested materials to pass therethrough without directly contacting adjacent tissue. It is contemplated that the examples described herein may be utilized in the esophagus, as well as the gastrointestinal, vascular, urinary, biliary, tracheobronchial, or renal tracts, for example. In some instances, medical device 10 (e.g., an esophageal stent, an intestinal stent, a vascular stent, tracheal stent, bronchial stent, etc.) may include an expandable scaffold.

Medical device 10 may include a stent 12 and a support structure 20. As will be described in greater detail below, stent 12 may be attached to a portion of support structure 20. Further, support structure 20 may permit stent 12 to move longitudinally (e.g., axially displace) within a body lumen to accommodate peristaltic motion.

Stent 12 may include an expandable scaffold. The expandable scaffold of stent 12 may have a first portion 14 and a second portion 16 positioned opposite first portion 14. When positioned in a body lumen (e.g., esophagus) first portion 14 may be defined as the end of stent 12 closest to a patient's mouth and second portion 16 may be defined as the end of stent 12 closest to a patient's stomach.

In some instances, first portion 14 may extend to a first or proximal end of the stent 12 and second portion 16 may extend to a second or distal end of stent 12 opposite the first end 14. First portion 14 may be attached to second portion 16 along the length of stent 12 to form an expandable tubular framework or scaffold with open ends and defining a lumen 15 extending therein. First portion 14 and/or second portion 16 may include a flared portion, such as a flared end region, if desired. For example, FIG. 1 illustrates first portion 14 having a flared end region 17 and second portion 16 having a flared end region 19. Additionally, first portion 14 and second portion 16 may extend along a central longitudinal axis of stent 12. In some instances, first portion 14 and second portion 16 may be cylindrical portions having a substantially constant diameter with flared end region 17 and flared end region 19 flaring outward therefrom to the first end and second end of stent 12, respectively.

A plurality of strut members 18 may be arranged in a variety of different designs and/or geometric patterns to form the expandable tubular framework or scaffold of stent 12. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 18 combined to form a rigid and/or semi-rigid stent structure. In some examples disclosed herein, the collection of strut members 18 forming a rigid and/or semi-rigid framework structure may be referred to as a scaffold. For example, strut members 18 may be wires or filaments braided, intertwined, interwoven, weaved, knitted, crocheted or the like to form the expandable scaffold or framework of stent 12. The strut members (e.g., wires or filaments) 18 of stent 12 may be configured to self-expand to an expanded diameter when unconstrained. Alternatively, strut members 18 may be formed from a monolithic structure (e.g., a cylindrical tubular member), such as a single, cylindrical tubular laser-cut Nitinol tubular member, in which the remaining portions of the tubular member form the strut members 18. The monolithic structure of stent 12 may be configured to self-expand to an expanded diameter when unconstrained.

Expandable scaffold of stent 12 in at least some examples disclosed herein may be constructed from a variety of materials. For example, expandable scaffold of stent 12 may be constructed from a metal (e.g., Nitinol). In other instances, expandable scaffold of stent 12 may be constructed from a polymeric material (e.g., PET). In yet other instances, expandable scaffold of stent 12 may be constructed from a combination of metallic and polymeric materials. Additionally, expandable scaffold of stent 12 or portions thereof may include a bioabsorbable and/or biodegradable material.

In some instances, it may be desirable to design stent 12 to include a covered portion. For example, stent 12 may include one or more layers (e.g., covering, coating, etc.) of material positioned on and/or adjacent to the outer and/or inner surface of the expandable scaffold (e.g., strut members 18). Further, an example covering may span the interstices between struts 18 of the expandable framework or scaffold of stent 12. In some instances, the covering may be a circumferential covering extending around the perimeter of the expandable framework or scaffold of stent 12 and extend continuously from the first end to the second end of stent 12, forming a fully-covered stent. In some instances, the covering may include an elastomeric or non-elastomeric material. In other instances, the covering may be formed from a suitable material, such as a biostable material. For example, the covering may be a polymeric material, such as silicone, polytetrafluoroethylene, polyurethane, or the like, or other materials including those disclosed herein. Further, the covering may be a biostable material. For purposes of discussion herein, a biostable material may be defined as a material that does not biodegrade.

As illustrated in FIG. 1, medical device 10 may include a support structure 20. In at least some examples, support structure 20 may be formed into annular shape, such as the shape of a torus. In other words, support structure 20 may be defined, geometrically, by revolving a cross-sectional perimeter of support structure 20 (taken in a plane parallel to and passing through the longitudinal axis of stent 12) about the longitudinal axis of stent 12. As shown in FIG. 1, in some instances the cross-sectional perimeter of torus-shaped support structure 20 may be substantially circular, however, it is contemplated that support structure 20 may have a variety of cross-sectional shapes (e.g., ovular, pear-shaped, rectangular, tear-drop, triangular, etc.), if desired.

Similar to the structure of stent member 12, support structure 20 may include a plurality of strut members 22 that may be arranged in a variety of different designs and/or geometric patterns to form the expandable tubular framework or scaffold of support structure 20. In some examples, support structure 20 may include a self-expanding structure. Numerous designs, patterns and/or configurations for the cell openings, strut thicknesses, strut designs, cell shapes are contemplated and may be utilized with embodiments of the support structure 20 or other support structures disclosed herein. Further, support structure 20 or other support structures disclosed herein may include structures having one or more strut members 22 combined to form a rigid and/or semi-rigid annular structure. In some examples disclosed herein, the collection of strut members 22 forming a rigid and/or semi-rigid framework structure may be referred to as a scaffold. For example, strut members 22 may be wires or filaments braided, intertwined, interwoven, weaved, knitted, crocheted or the like to form the expandable scaffold or framework of support structure 20. The strut members (e.g., wires or filaments) 22 of support structure 20 may be configured to self-expand to an expanded diameter when unconstrained. Alternatively, strut members 22 may be formed from a monolithic structure (e.g., a cylindrical tubular member), such as a single, cylindrical tubular laser-cut Nitinol tubular member, in which the remaining portions of the tubular member form the strut members 22. The monolithic structure of support structure 20 may be configured to self-expand to an expanded diameter when unconstrained.

Support member 20 in at least some examples disclosed herein may be constructed from a variety of materials. For example, expandable scaffold of support member 20 may be constructed from a metal (e.g., Nitinol). In other instances, expandable scaffold of support member 20 may be constructed from a polymeric material (e.g., PET). In yet other instances, expandable scaffold of support member 20 may be constructed from a combination of metallic and polymeric materials. Additionally, expandable scaffold of support member 20 or portions thereof may include a bioabsorbable and/or biodegradable material.

In some instances, it may be desirable to design support member 20 to include a covered portion. For example, support member 20 may include one or more layers (e.g., covering, coating, etc.) of material positioned on and/or adjacent to the outer and/or inner surface of strut members 22. Further, an example covering may span the interstices between struts 22 of the expandable framework of scaffold of support member 20. In some instances, the covering may include an elastomeric or non-elastomeric material. In other instances, the covering may be formed from a suitable material, such as a biostable material. For example, the covering may be a polymeric material, such as silicone, polytetrafluoroethylene, polyurethane, or the like, or other materials including those disclosed herein. Further, the covering may be a biostable material. For purposes of discussion herein, a biostable material may be defined as a material that does not biodegrade.

FIG. 1 further illustrates that stent member 12 may extend through a centrally positioned opening (e.g., aperture) defined by the torus shaped support structure 20. In other words, torus 20 may extend (e.g., radially extend) around the outer perimeter (e.g., the outer surface) of stent member 12.

Figure 2:
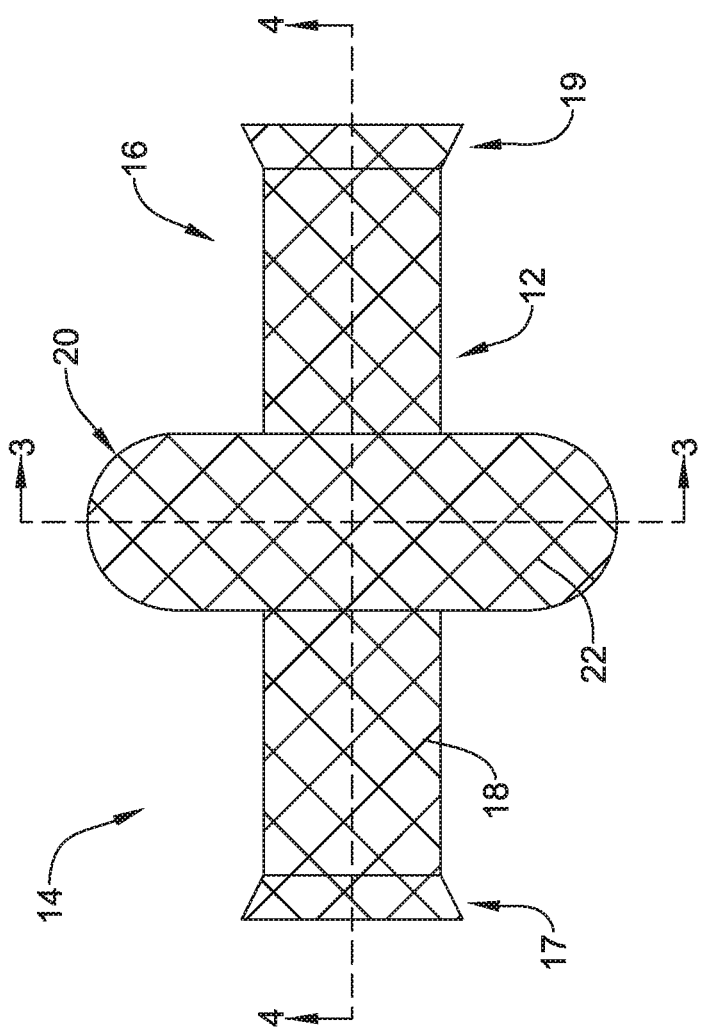
FIG. 2 illustrates a side view of the stent including a support structure shown in FIG. 1.

FIG. 2 illustrates that support member 20 may be positioned along the outer surface of stent member 12 between first portion 14 and second portion 16. While FIG. 2 shows support structure 20 positioned substantially at a midpoint between first portion 14 and second portion 16, it is contemplated that support structure 20 may be positioned at any point along the longitudinal axis of stent member 12. For example, support structure 20 may be positioned closer to the first end or closer to the second end of stent member 12.

Figure 3:
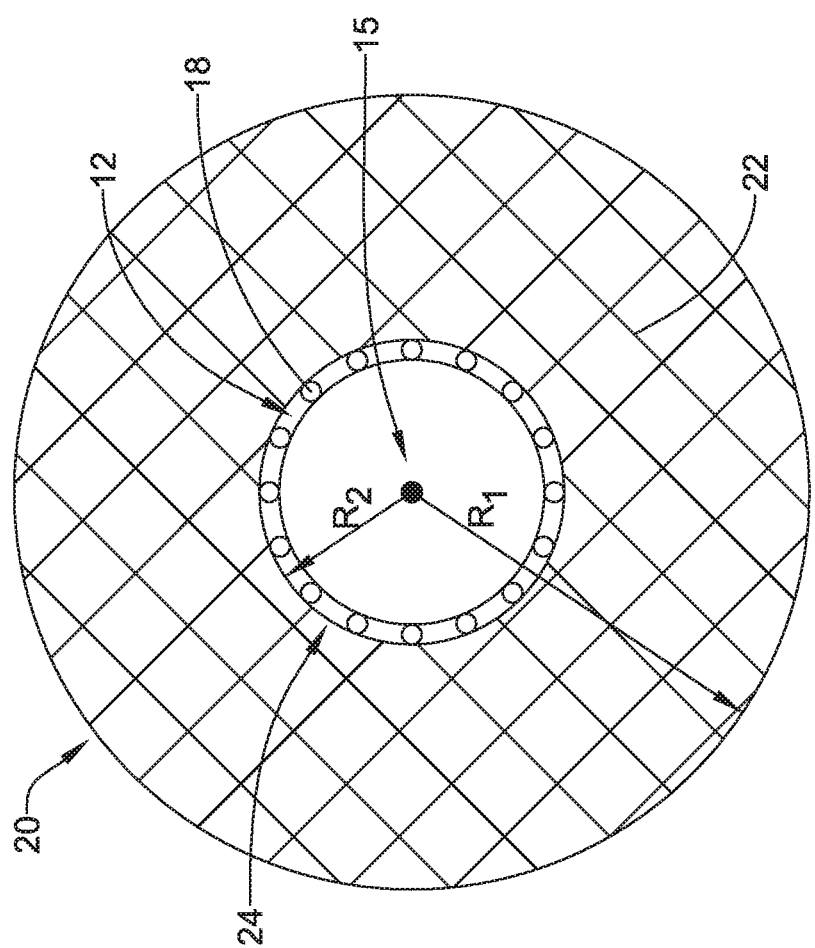
FIG. 3 illustrates a cross-sectional view along line 3-3 of FIG. 2.

FIG. 3 illustrates a cross-sectional view of medical device 10 along line 3-3 of FIG. 2. FIG. 3 further illustrates the cross-sectional shape of the torus-shaped support structure 20 described above. For example, FIG. 3 shows torus 20 having an outer circumference shaped as a circle. In FIG. 3, the radius defining the outer circumference of torus 20 is depicted as "$R_1$." Additionally, FIG. 3 shows torus 20 including an inner circle 24 corresponding to the centrally positioned aperture of torus 20. In FIG. 3, the radius defining the inner aperture of torus 20 is depicted as "$R_2$." Further, FIG. 3 illustrates strut members 22 which are combined together to define support structure 20.

FIG. 3 further illustrates the strut members 18 which define stent member 12. Further, as discussed above, FIG. 3 illustrates strut members 18 arranged circumferentially such that they define a lumen 15 extending axially throughout the length of stent member 12. As discussed above, FIG. 3 further illustrates that stent member 12 may be positioned within the centrally positioned aperture of support structure 20 such that support structure 20 circumferentially surrounds stent member 12. As shown in FIG. 3, the circumference of the aperture of torus 20 (e.g., the circle defined by radius $R_2$) may encircle the outer circumference (e.g., the outer surface) of stent member 12.

Figure 4:
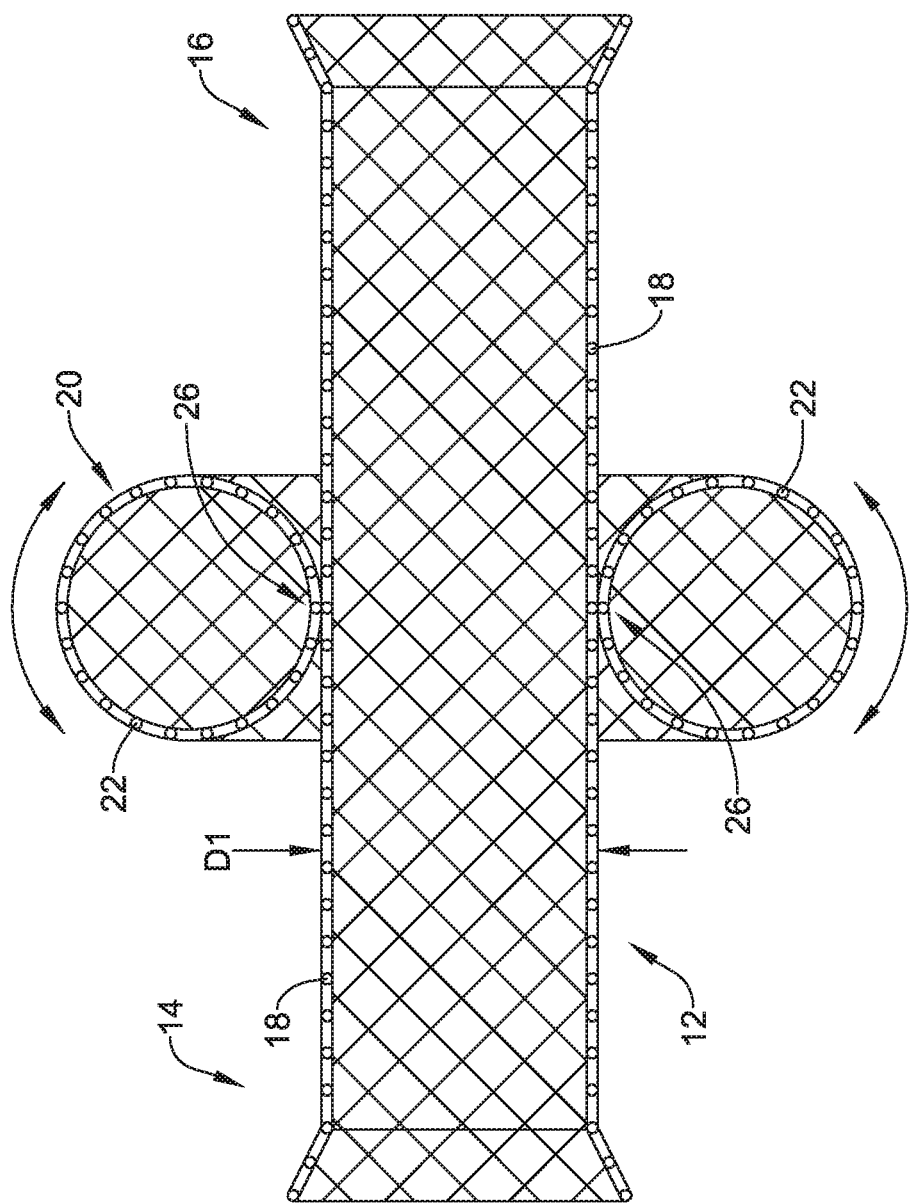
FIG. 4 illustrates a cross-sectional view along line 4-4 of FIG. 2.

FIG. 4 illustrates a cross-sectional view of medical device 10 along line 4-4 of FIG. 2. FIG. 4 further illustrates that the cross-sectional shape of the torus-shaped support member 20 taken in a plane parallel to and passing through the longitudinal axis of stent member 12 may be substantially circular. Additionally, FIG. 4 provides another example illustrating that torus member 20 may extend around the outer surface of stent member 12. As discussed above, FIG. 4 illustrates that stent member 12 may extend through the aperture of torus member 20. Further, FIG. 4 provides another example that shows that the diameter of the inner aperture of torus 20 (defined by radius $R_2$ in FIG. 3) may be sized to engage the outer diameter of stent member 12 (depicted as $D_1$ in FIG. 4).

Additionally, FIG. 4 illustrates an engagement location 26 depicting the location at which the surface of support member 20 engages (e.g., attaches to) the outer surface of stent member 12. It can be appreciated that the support member 20 may be attached to stent member 12 at one or more locations 26. For example, support member 20 may be attached to stent member 12 at 1, 2, 3, 4, 5, 6, 7, 8, 9, 10, 15, 20, or more attachment locations. Further, it is contemplated that support member 20 may be attached to stent member 12 along the entire circumference of stent member 12, if desired.

While not illustrated in the Figures, it can be appreciated that stent member 12 may be attached to support structure 20 using a variety of methodologies. For example, in some instances the filaments 22 of support member 20 may be unitary portions (e.g. extensions) of filaments 18 forming stent member 12. In other instances, the filaments 18 of stent member 12 may be interwoven, braided, knitted, combined, etc. with the filaments 22 of support member 20. Additionally, it can be appreciated that the filaments 18 of stent member 12 may be welded, sintered, melted, etc. with the filaments 22 of support member 20. Further, the filaments 22 of support member 20 and the filaments 18 of stent 20 may be combined and/or joined at one or more locations 26.

It can be appreciated that support member 20 may be attached to stent 20 along a substantially circumferential line extending around the circumference of stent 12. Additionally, it can be appreciated due to the substantially annular cross-sectional shape of supporting member 20, support member 20 may able to pivot (e.g., partially rotate, roll, shift, etc.) along the outer surface of stent 12. For example, as depicted by the double-ended arrows of FIG. 4, the torus shaped supporting member 20 may pivot around attachment location 26.

Further, it is noted that while the above discussion has focused on supporting member 20 (e.g., torus-shaped supporting member 40) being substantially circular in cross-section, it is contemplated that supporting member may be a variety of cross-sectional shapes (e.g., ovular, pear-shaped, tear-drop, triangular, etc.) Similar to that discussed above, some of those shapes may permit supporting member 20 to pivot/rotate along the outer surface of stent member 12. Additionally, it is contemplated that the construction of supporting member 20 may permit it to be deformed as it rotates and/or pivots around attachment location 26. For example, when deployed in a body lumen, supporting member 20 may deform as it rotates and/or pivots around attachment location 26.

Figure 5A:
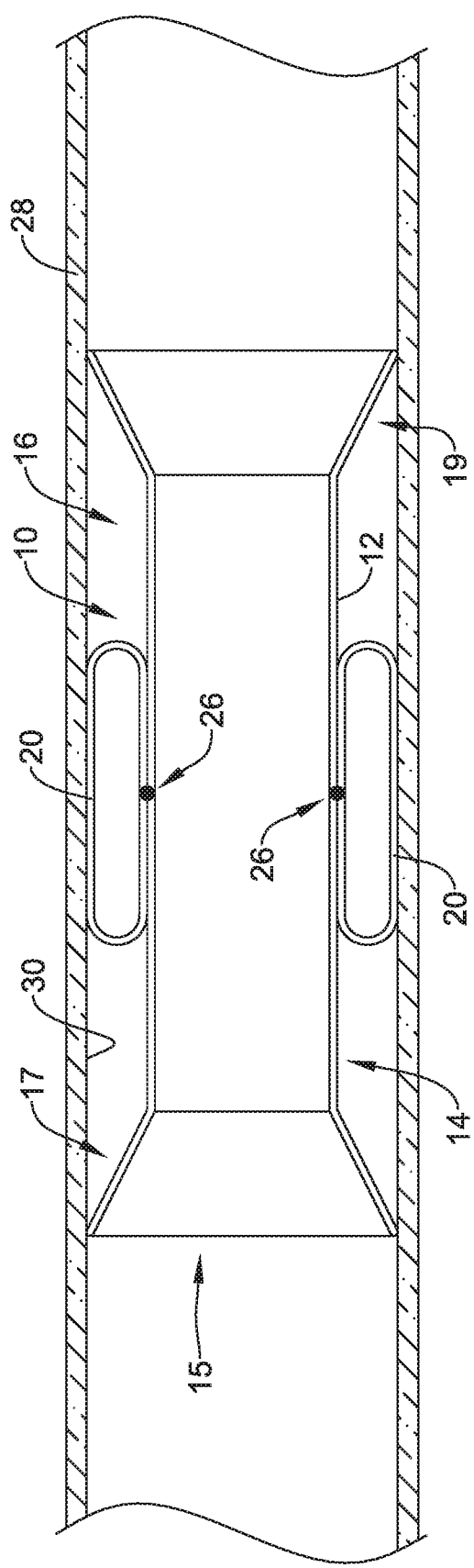
FIGS. 5A-5C illustrate an example stent including a support structure positioned within a body lumen at different positions during peristalsis.

FIG. 5A shows example medical device 10 deployed in body lumen 28. As illustrated, upon initial deployment in the body lumen 28, the flared portion 17 of the first region 14 and flared portion 19 of the second region 16 may apply a radially outward force upon the inner surface of body lumen 28 as the expandable scaffold of stent 12 expands to an expanded state in the body lumen 28. This radially outward force exerted on the inner surface of body lumen 28 may provide a temporary resistance to migration of medical device 10 within the body lumen 28. Further, deployment and expansion of support member 20 may apply a radially outward force upon the inner surface of body lumen 28.

Additionally, the flared portions 17/19 of first portion 14 and second portion 16 may permit the flared portions of stent 12 to contact the tissue on the inner surface of body lumen 28. This contact of the flared portions 17/19 with the tissue of the inner surface of the body lumen 28 may provide a seal that funnels food or other material through lumen 15 of stent 12. For example, as food or other material travels down the esophagus, the flared portion 17 of stent 12 may prevent the food from traveling along the exterior of stent 12 and along the inner surface of body lumen 28 whereby it might encounter support member 20. Rather, flared portion 17 is designed to provide a circumferential seal around the inner surface of body lumen 28 such that the food is directed through the lumen 15 of stent 12. As discussed above, the inner surface of stent 12 may include a covering which fully covers stent 12 and creates a pathway through which food and other material may travel (without leaking to the outer surface of stent 12).

Further, FIG. 5A illustrates that, after deployment, the supporting member 20 may be positioned between the outer surface of stent member 12 and the inner surface of body lumen 28. For example, as illustrated in FIG. 5A, supporting member 20 may be positioned such that it spaces stent member 12 away from the inner surface 30 of body lumen 28. As illustrated above, in at least some examples support member 20 may surround stent member 12 (such as the example shown in FIG. 5A) such that at least the portion of stent member 12 located adjacent the support member 20 is positioned away from the inner surface 30 of body lumen 28.

As discussed above, in some instances it may be desirable to design medical device 10 to move within body lumen 28. For example, when deployed in the esophagus, it may be desirable to design medical device 10 so that it can respond to the forces imparted by the peristaltic movement of the esophagus. The peristaltic movement of the esophagus may impart forces which radially "squeeze" one or more portions of medical device 10. Further, these radial squeezing forces may push medical device 10 along the esophagus in the axial direction. In other words, the peristaltic motion may resemble a rolling wave of radial contraction that attempts to move medical device 10 along the longitudinal axis of the esophagus (from a position closer to a patient's mouth to a position farther from a patient's mouth).

Figure 5B:
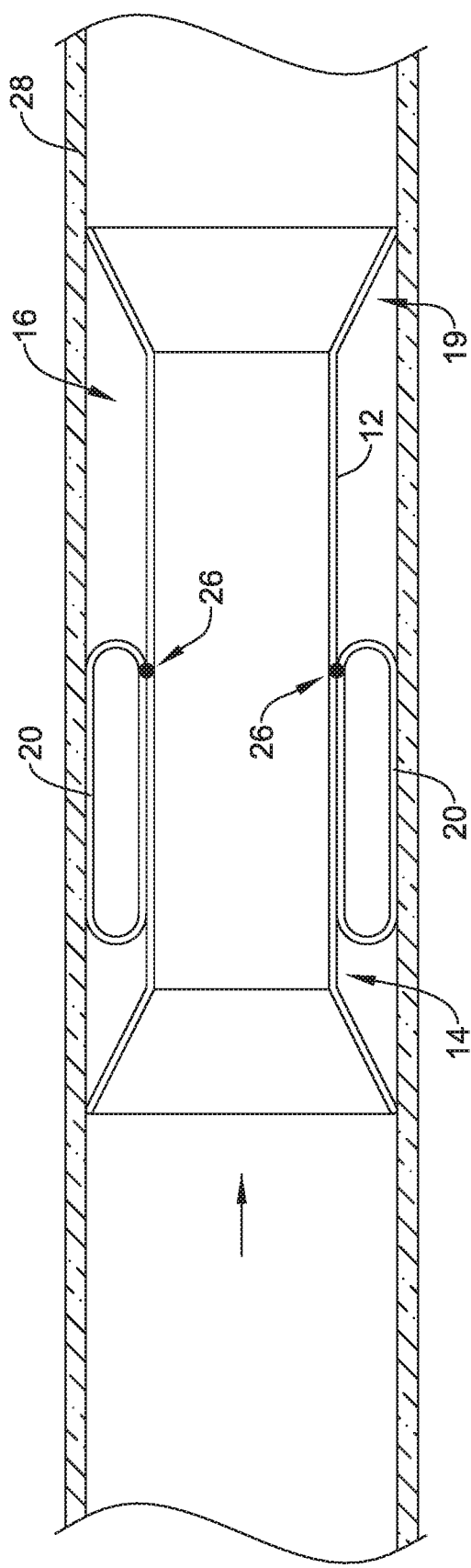

Therefore, as discussed above, in at least some examples, it may be beneficial to design medical device 10 such that stent 12 has the ability to temporarily shift (e.g., move, deflect, etc.) longitudinally along the body lumen 28 (e.g., esophagus). FIG. 5B illustrates an arrow showing the direction in which peristaltic forces, and hence, medical device 10 has shifted along the longitudinal axis. FIG. 5B further illustrates that in at least some examples, the ability of stent 12 to shift and/or translate longitudinally along body lumen 28 is due to the ability of supporting member 20 to "roll" along a portion of body lumen 28 (and the outer surface of stent 12). For example, the rolling motion of supporting member 20 (which results in the longitudinal displacement of stent 12) can be appreciated by comparing the location of supporting member 20 in FIGS. 5A and 5B relative to stent 12. It can be seen in FIGS. 5A and 5B that as stent 12 shifts along the axis (in the direction of the arrow shown in FIG. 5B), that supporting member 20 rolls upon itself such that the majority of supporting member 20 is positioned adjacent the first portion 14 of stent member 12.

Figure 5C:
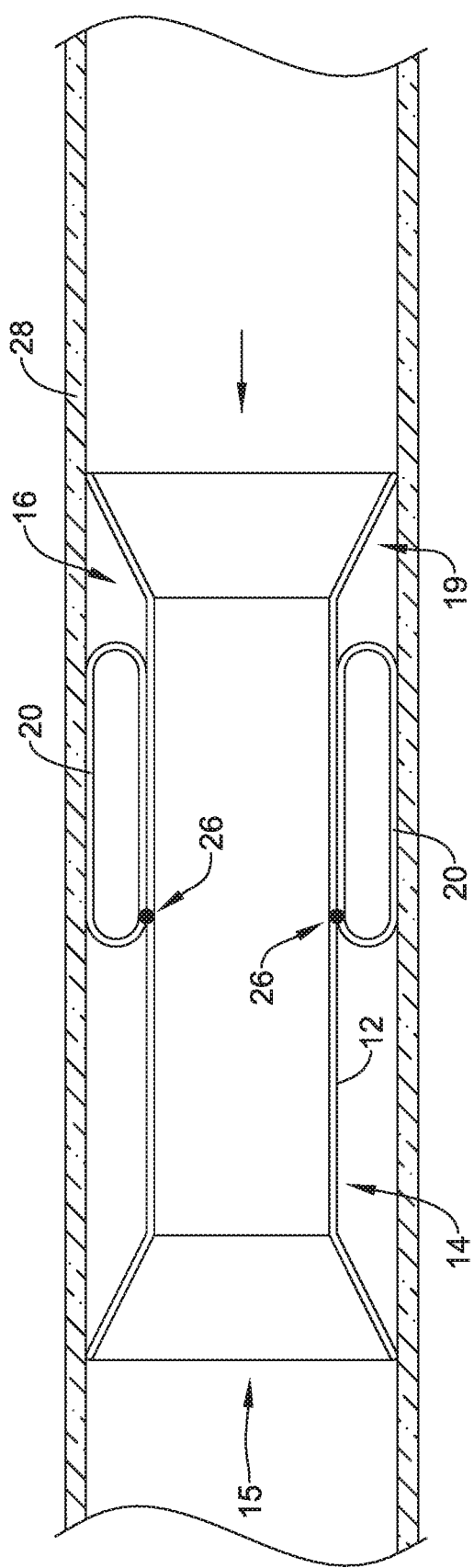

Similarly, FIG. 5C illustrates stent member 12 shifting along the longitudinal axis in a direction opposite to that illustrated in FIG. 5B. (e.g., in a direction depicted by the arrow in FIG. 5C). It can be appreciated that supporting member 20 may facilitate the movement of stent 12 longitudinally along body lumen 28 by rolling in a direction opposite that described in FIG. 5B. As shown in FIG. 5C, the rolling motion of supporting member 20 (which results in the longitudinal displacement of stent 12) can be appreciated by comparing the location of supporting member 20 in FIGS. 5B and 5C relative to the stent 12. It can be seen in FIGS. 5B and 5C that as stent 12 moves along the axis (in the direction of the arrow shown in FIG. 5C), that supporting member 20 rolls upon itself such that the majority of supporting member 20 is positioned adjacent the second portion 16 of stent member 12.

Figure 6:
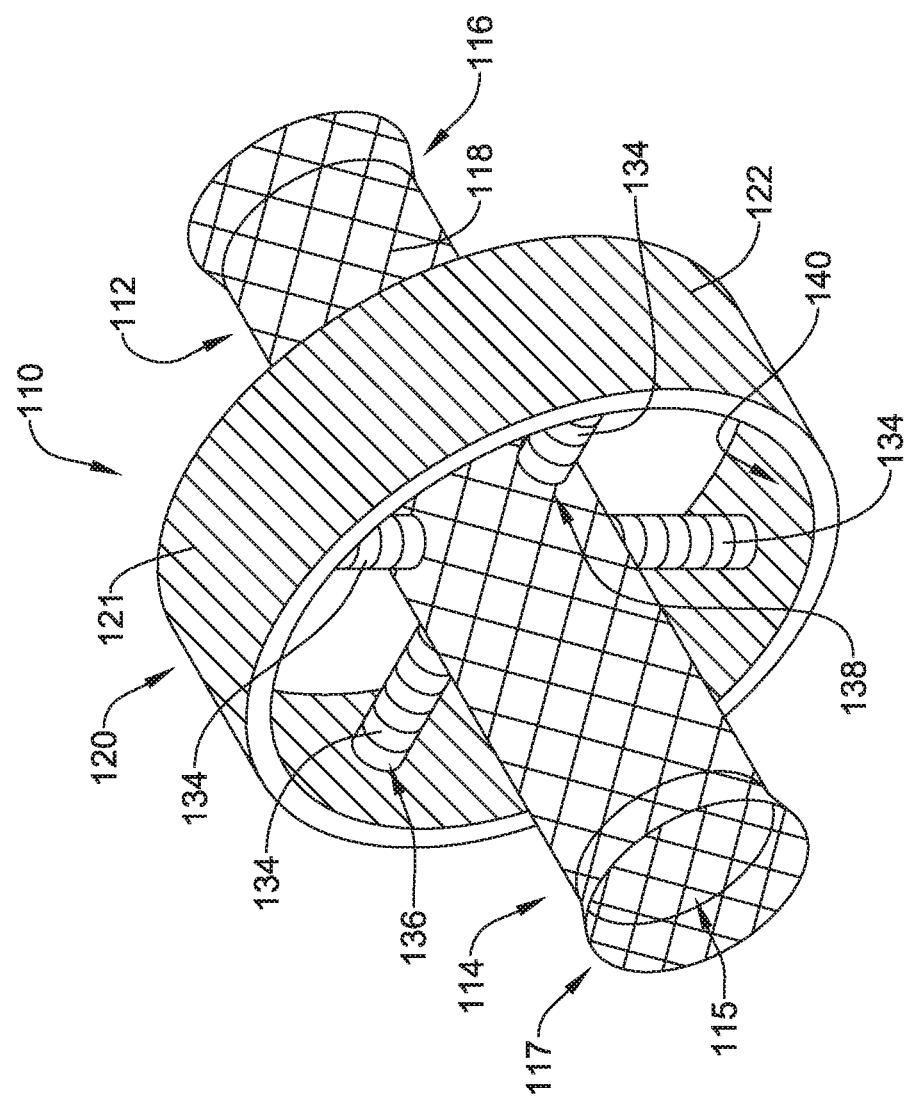
FIG. 6 illustrates another example stent including a support structure.

FIG. 6 illustrates another example medical device 110. Medical device 110 may include a stent 112 and a support structure 120. As will be described in greater detail below, stent 112 may be attached to a portion of support structure 120. Further, support structure 120 may permit stent 112 to move (e.g., axially displace) within a body lumen.

Stent 112 may include an expandable scaffold. The expandable scaffold of stent 112 may have a first portion 114 and a second portion 116 positioned opposite portion 114. When positioned in a body lumen (e.g., esophagus) first portion 114 may be defined as the end of stent 112 closest to a patient's mouth and second portion 116 may be defined as the end of stent 112 closest to a patient's stomach.

In some instances, first portion 114 may extend to a first end of the stent 112 and second portion 116 may extend to a second end of stent 112 opposite the first end. First portion 114 may be attached to second portion 116 along the length of stent 112 to form an expandable tubular framework or scaffold with open ends and defining a lumen 115 extending therein. First portion 114 and/or second portion 116 may include a flared end region, if desired. For example, FIG. 6 illustrates first portion 114 having a flared end region 117 and second portion 116 having a flared end region 119. Additionally, first portion 114 and second portion 116 may extend along a central longitudinal axis of stent 112. In some instances, first portion 114 and second portion 116 may be cylindrical portions having a substantially constant diameter with flared end region 117 and flared end region 119 flaring outward therefrom to the first end and second end of stent 112, respectively.

A plurality of strut members 118 may be arranged in a variety of different designs and/or geometric patterns to form the expandable tubular framework or scaffold of stent 112. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 118 combined to form a rigid and/or semi-rigid stent structure. In some examples disclosed herein, the collection of strut members 118 forming a rigid and/or semi-rigid framework structure may be referred to as a scaffold. For example, strut members 118 may be wires or filaments braided, intertwined, interwoven, weaved, knitted, crocheted or the like to form the expandable scaffold or framework of stent 112. The strut members (e.g., wires or filaments) 118 of stent 112 may be configured to self-expand to an expanded diameter when unconstrained. Alternatively, strut members 118 may be formed from a monolithic structure (e.g., a cylindrical tubular member), such as a single, cylindrical tubular laser-cut Nitinol tubular member, in which the remaining portions of the tubular member form the strut members 118. The monolithic structure of stent 112 may be configured to self-expand to an expanded diameter when unconstrained.

Expandable scaffold of stent 112 in at least some examples disclosed herein may be constructed from a variety of materials. For example, expandable scaffold of stent 112 may be constructed from a metal (e.g., Nitinol). In other instances, expandable scaffold of stent 112 may be constructed from a polymeric material (e.g., PET). In yet other instances, expandable scaffold of stent 112 may be constructed from a combination of metallic and polymeric materials. Additionally, expandable scaffold of stent 112 or portions thereof may include a bioabsorbable and/or biodegradable material.

In some instances, it may be desirable to design stent 112 to include a covered portion. For example, stent 112 may include one or more layers (e.g., covering, coating, etc.) of material positioned on and/or adjacent to the outer and/or inner surface of the expandable scaffold (e.g., strut members 118). Further, an example covering may span the interstices between struts 118 of the expandable framework or scaffold of stent 112. In some instances, the covering may be a circumferential covering extending around the perimeter of the expandable framework or scaffold of stent 112 and extend continuously from the first end to the second end of stent 112, forming a fully-covered stent. In some instances, the covering may include an elastomeric or non-elastomeric material. In other instances, the covering may be formed from a suitable material, such as a biostable material. For example, the covering may be a polymeric material, such as silicone, polytetrafluoroethylene, polyurethane, or the like, or other materials including those disclosed herein. Further, the covering may be a biostable material. For purposes of discussion herein, a biostable material may be defined as a material that does not biodegrade.

As illustrated in FIG. 6, medical device 110 may include a support structure 120. In at least some examples, support structure 120 may include a support ring 121 encircling stent 112 and one or more support arms 134 extending radially between stent 112 and support ring 121. In other words, support ring 121 may extend around the outer surface of stent 112, while support arms 134 may space support ring 121 away from the outer surface of stent 112.

Similar to the structure of stent member 112, support structure 120 may include a plurality of strut members 122 that may be arranged in a variety of different designs and/or geometric patterns to form the expandable tubular framework or scaffold of support ring 121. Numerous designs, patterns and/or configurations for the cell openings, strut thicknesses, strut designs, cell shapes are contemplated and may be utilized with embodiments of the support ring 121 or other support structures disclosed herein. In some examples disclosed herein, the collection of strut members 122 forming a rigid and/or semi-rigid framework structure may be referred to as a scaffold. For example, strut members 122 may be wires or filaments braided, intertwined, interwoven, weaved, knitted, crocheted or the like to form the expandable scaffold or framework of support ring 121. The strut members (e.g., wires or filaments) 122 of support ring 121 may be configured to self-expand to an expanded diameter when unconstrained. Alternatively, strut members 122 may be formed from a monolithic structure (e.g., a cylindrical tubular member), such as a single, cylindrical tubular laser-cut Nitinol tubular member, in which the remaining portions of the tubular member form the strut members 122. The monolithic structure of support structure 120 may be configured to self-expand to an expanded diameter when unconstrained.

In other examples, support ring 121 may be formed of a solid, monolith material. For example, support member 120 may be formed as a single, solid layer of material formed into the shape of a ring as shown in FIG. 6. Further, it is contemplated that a support ring 121 may further include reinforcing filaments and/or strut members.

As discussed above, FIG. 6 illustrates support ring 121 spaced away from stent member 112 by one or more support arms 134. As shown in FIG. 6, each of the one or more support arms 134 may include a first end 136 attached to an inner surface 140 of support ring 121 and a second end 138 attached to an outer surface of stent member 112. FIG. 6 further illustrates that support arms 134 may be spaced away from one another (e.g., circumferentially spaced away from one another along the outer surface of stent 112). However, it is contemplated that support arms 134 may be both spaced in a variety of configurations around the outer surface of stent member 112 and attached to the inner surface 140 in a variety of configurations.

Similar to the structure of stent member 112 and support ring 121, support arms 134 may include a plurality of strut members that may be arranged in a variety of different designs and/or geometric patterns to form the expandable tubular framework or scaffold of support arms 134. Numerous designs, patterns and/or configurations for the stent cell openings, strut thicknesses, strut designs, stent cell shapes are contemplated and may be utilized with embodiments of the support arms 134 or other support structures disclosed herein. In some examples disclosed herein, the collection of strut members forming a rigid and/or semi-rigid framework structure may be referred to as a scaffold. For example, support arms 134 may be wires or filaments braided, intertwined, interwoven, weaved, knitted, crocheted or the like to form the expandable scaffold or framework of support arms 134. The strut members (e.g., wires or filaments) of support arms 134 may be configured to self-expand to an expanded diameter when unconstrained.

In other examples, support members 134 may be formed of a solid, monolith material. For example, support members 134 may formed as a single, solid material formed into the shape of the support arms shown in FIG. 6. Further, it is contemplated that support arms 134 may further include reinforcing filaments and/or strut members. The monolithic structure of support members 134 may be configured to self-expand when unconstrained.

Both support ring 121 and support arms 134 in at least some examples disclosed herein may be constructed from a variety of materials. For example, expandable scaffold of support member 120 and support arms 134 may be constructed from a metal (e.g., Nitinol). In other instances, expandable scaffold of support member 120 and support arms 134 may be constructed from a polymeric material (e.g., PET). In yet other instances, support members 134 may be constructed from a combination of metallic and polymeric materials. Additionally, support members 134 or portions thereof may include a bioabsorbable and/or biodegradable material.

In some instances, it may be desirable to design support members 134 to include a covered portion. For example, support members 134 may include one or more layers (e.g., covering, coating, etc.) of material positioned on and/or adjacent to the outer and/or inner surface of support members 134. In some instances, the covering may include an elastomeric or non-elastomeric material. In other instances, the covering may be formed from a suitable material, such as a biostable material. For example, the covering may be a polymeric material, such as silicone, polytetrafluoroethylene, polyurethane, or the like, or other materials including those disclosed herein. Further, the covering may be a biostable material. For purposes of discussion herein, a biostable material may be defined as a material that does not biodegrade.

FIG. 6 further illustrates that stent member 112 may be positioned in a central region of support ring 121. In other words, support ring 121 may extend around the outer surface of stent member 112, whereby the length of individual support arms 134 and the spacing of support arms 134 may determine the precise positioning of stent member 112 within support ring 121. It is contemplated that stent 112 may be positioned in a variety of positions within support ring 121.

Figure 7:
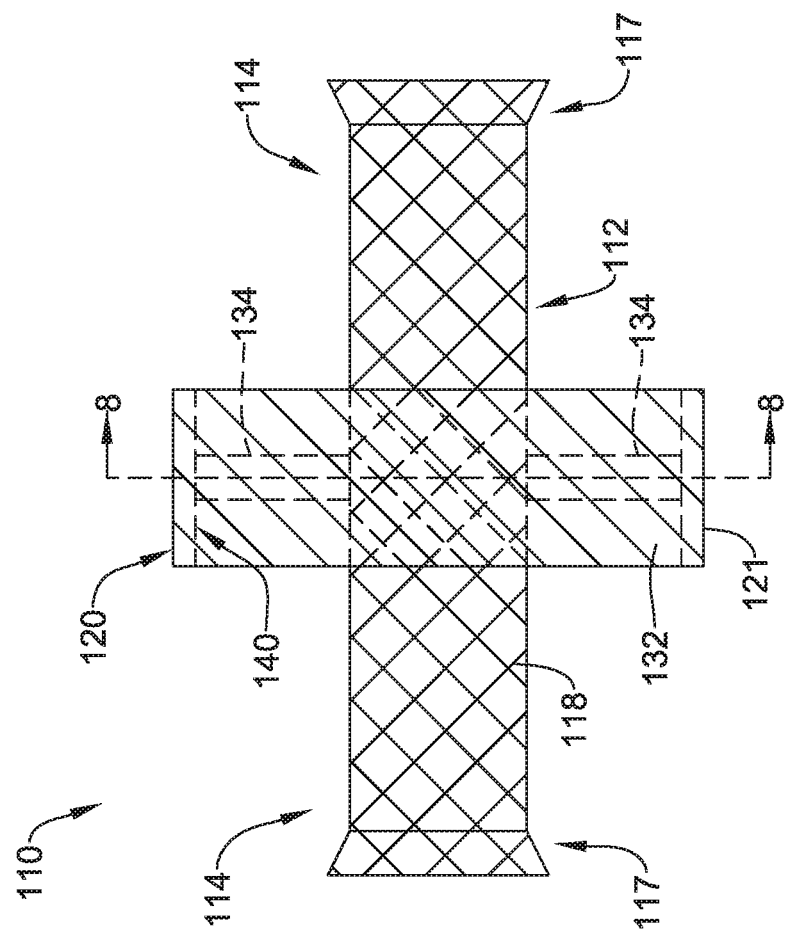
FIG. 7 illustrates a side view of the stent including a support structure shown in FIG. 6.

FIG. 7 illustrates that support member 120 may be positioned along the outer surface of stent member 112 between first portion 114 and second portion 116. While FIG. 7 shows support structure 120 positioned substantially at a midpoint between first portion 114 and second portion 116, it is contemplated that support structure 120 may be positioned at any point along the longitudinal axis of stent member 112. For example, support structure 120 may be positioned closer to first end of stent 112 or closer to second end of stent 112. Further, FIG. 7 shows support arms 134 extending radially from an inner surface 140 of support 120 and attaching to an outer surface of stent member 112.

Figure 8:
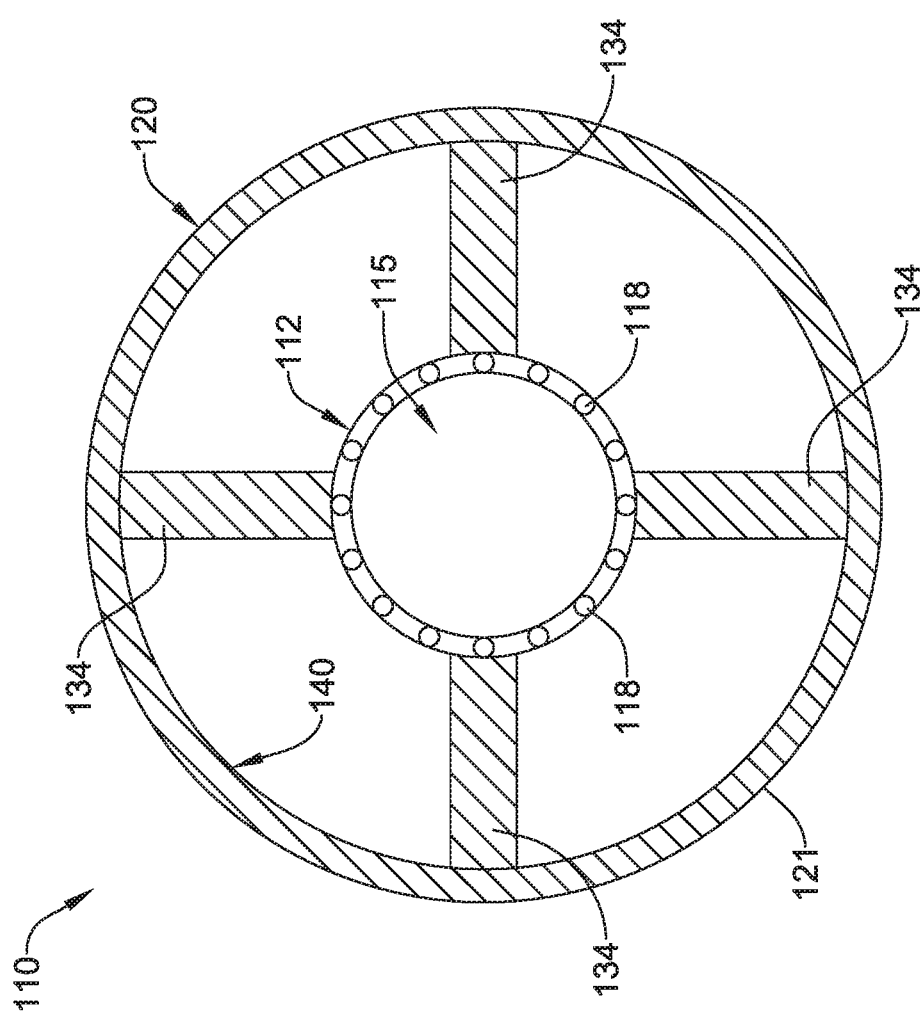
FIG. 8 illustrates a cross-sectional view along line 8-8 of FIG. 6.

FIG. 8 illustrates a cross-sectional view of medical device 110 along line 8-8 of FIG. 7. As described above, FIG. 8 illustrates supporting ring 121 encircling (e.g., extending around) the outer surface of stent member 112. For example, FIG. 8 shows support ring 120 having a substantially circular cross-sectional shape. Further, FIG. 8 shows support arms 134 extending from the inner surface 140 of support ring 121 to the outer surface of stent member 112.

FIG. 8 further illustrates the strut members 118 which define stent member 112. Further, as discussed above, FIG. 8 illustrates strut members 118 arranged circumferentially such that they define a lumen 115 extending along the length of stent member 112. As discussed above, FIG. 8 further illustrates that stent member 112 may be positioned in a central region of support ring 121.

As described above, it can be appreciated that support arms 134 may be attached to support structure 120 and/or stent member 112 using a variety of methodologies. For example, the support arms 134 may be interwoven, braided, knitted, combined, etc. with the filaments and/or monolith structure 122 of support member 120 and/or filaments 118 of stent member 112. Additionally, it can be appreciated that the support arms 134 may be welded, sintered, melted, etc. with the filaments and/or monolith structure 122 of support member 120 and/or filaments 118 of stent member 112.

Figure 9A:
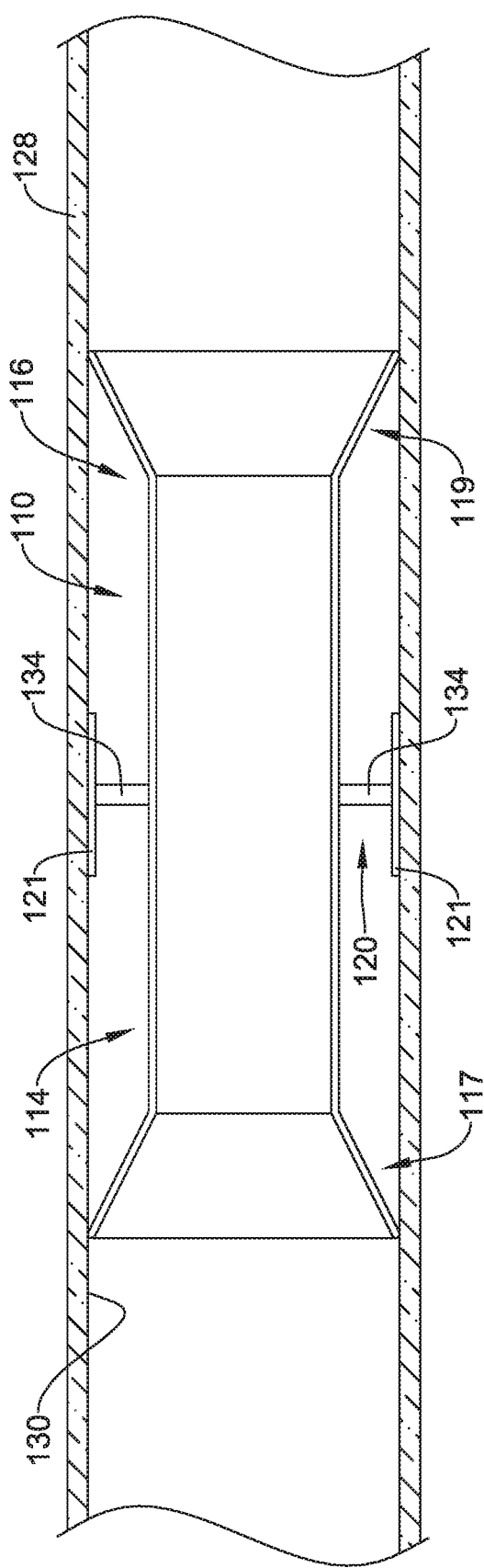
FIGS. 9A and 9B illustrate an example stent including a support structure positioned within a body lumen at different positions during peristalsis.

FIG. 9A shows example medical device 110 deployed in body lumen 128. Similarly to that described with respect to FIG. 5A above, upon initial deployment in the body lumen 128, the flared portion 117 of the first region 114 may apply a radially outward force upon the inner surface of body lumen 128. This radially outward force exerted on the inner surface of body lumen 128 may provide a temporary resistance to migration of medical device 110 within to the body lumen 128. Further, following deployment of first portion 114, support member 120 may be deployed, followed by the deployment of second portion 116. The flared portion 119 of the second region 116 may apply a radially outward force upon the inner surface of body lumen 128. Similar to the flared portion 117 of first portion 114, the radially outward force exerted on the inner surface of body lumen 128 by flared portion 119 may provide a temporary resistance to migration of medical device 110 within the body lumen 128.

Additionally, the flared portions 117/119 of first portion 114 and second portion 116 may permit the flared portions of stent 112 to contact the tissue on the inner surface of body lumen 128. This contact of the flared portions 117/119 with the tissue of the inner surface 140 of the body lumen 128 may provide a seal that funnels food or other material through lumen 115 of stent 112. For example, as food or other material travels down the esophagus, the flared portion 117 of stent 112 may prevent the food from traveling along the inner surface of body lumen 128 whereby it might encounter support ring 121 and/or support arms 134. Rather, flared portion 117 is designed to provide a circumferential seal around the inner surface of body lumen 128 such that the food is directed through the lumen 115 of stent 112. As discussed above, the inner surface of stent 112 may include a covering which creates a pathway through which food and other material may travel (without leaking to the outer surface of stent 112).

Further, FIG. 9A illustrates that, after deployment, the support arms 134 and supporting ring 121 may be positioned between the outer surface of stent member 112 and the inner surface of body lumen 128. For example, as illustrated in FIG. 9A, supporting ring 121 may be positioned such that it spaces stent member 112 away from the inner surface 130 of body lumen 128. As illustrated above, in at least some examples support ring 121 may encircle stent member 112 (such as the example shown in FIG. 9A) such that at least the portion of stent member 112 located adjacent the support ring 121 is positioned away from the inner surface 130 of body lumen 128.

As discussed above, in some instances it may be desirable to design medical device 110 to shift (e.g., move, deflect, etc.) within body lumen 128. For example, when deployed in the esophagus, it may be desirable to design medical device 110 so that it can respond to the forces imparted by the peristaltic movement of the esophagus. As discussed above, the peristaltic movement of the esophagus may impart forces which radially "squeezes" one or more portions of medical device 110. Further, these radial squeezing forces may push medical device 110 along the esophagus in the longitudinal direction. In other words, the peristaltic motion may resemble a rolling wave of radial contraction that attempts to move medical device 110 along the longitudinal axis of the esophagus.

Figure 9B:
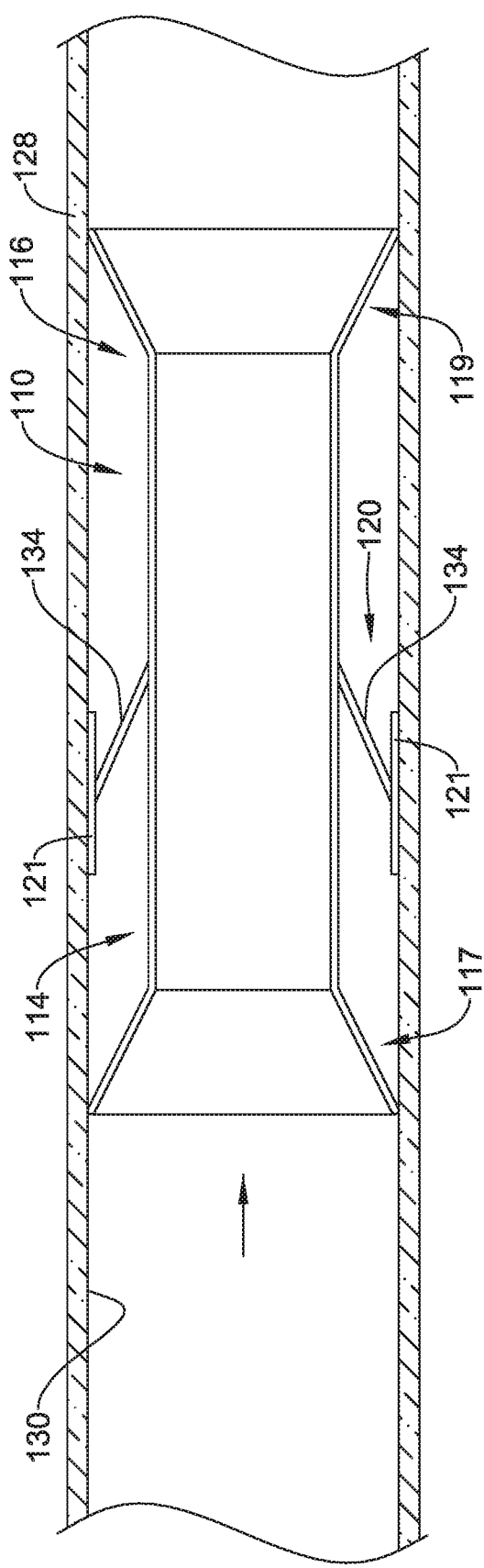

Therefore, as discussed above, in at least some examples, it may be beneficial to design medical device 110 such that stent 112 has the ability to temporarily shift (e.g., move, deflect) longitudinally relative to body lumen 128 (e.g., esophagus). For example, FIG. 9B illustrates an arrow showing the direction in which peristaltic forces, and hence, stent 112 has shifted relative to the longitudinal axis. FIG. 9B further illustrates that in at least some examples, the ability of stent 112 to translate longitudinally along body lumen 128 is due to the ability of support arms 134 to pivot, twist, rotate, flex and/or extend relative to at least a portion of body lumen 128. It is also contemplated that supporting arms 134 may radially deform (e.g., contract and/or extend radially inward and/or outward). Comparison of FIG. 9A to 9B shows that as the peristaltic forces translate down the esophagus, supporting ring 121 may remain stationary with respect to body lumen 128 while support arms 134 pivot, rotate, flex and/or extend relative to supporting member 120. This movement of support arms 134 permits stent 112 to shift along the longitudinal axis (as shown in FIG. 9A and FIG. 9B). It is noted that while the Figures do not illustrate stent 112 shifting back to the position shown in FIG. 9A, it is contemplated that stent 112 can shift back to the position show in 9A. It is further contemplated that stent 112 can shift in a direction opposite the direction shown in FIG. 9B.

Figure 10:
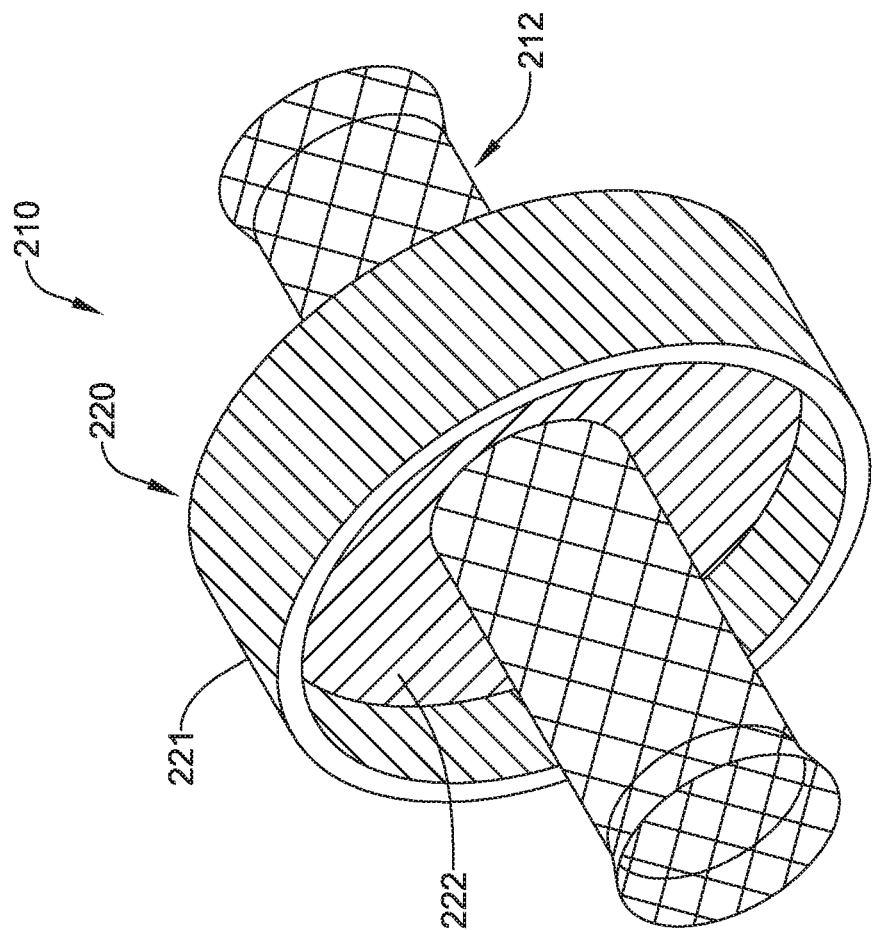
FIG. 10 illustrates another example stent including a support structure.

FIG. 10 illustrates another example medical device 210. Device 210 may be similar in form and function to the medical device 110 shown in FIG. 6. As shown in FIG. 10, medical device 210 may include a stent 212 and a supporting structure 220 circumferentially surrounding stent 212. Similar to the structure of stent and supporting member examples described above, support structure 220 may include support ring 221 and a wall 222 extending radially between support ring 221 and stent 212. Numerous designs, patterns and/or configurations for the stent cell openings, strut thicknesses, strut designs, stent cell shapes are contemplated and may be utilized with embodiments of the stent 212 and/or support structure 220. In some examples disclosed herein, the collection of strut members forming a rigid and/or semi-rigid framework structure may be referred to as a scaffold. For example, stent 212 and/or support member 220 may be formed of wires or filaments braided, intertwined, interwoven, weaved, knitted, crocheted or the like to form the expandable scaffold or framework of stent 212 and/or support structure 220. The strut members (e.g., wires or filaments) of stent 212 and/or support structure 220 may be configured to self-expand to an expanded diameter when unconstrained.

In other examples, support structure 220, including support ring 221 and wall 222, may be formed of a solid, monolith material. For example, support structure 220 may formed as a single, solid material formed into the shape of the support structure 220 shown in FIG. 10. Further, it is contemplated that support structure 220 may further include reinforcing filaments and/or strut members. The monolithic structure of support structure 220 may be configured to self-expand when unconstrained.

Both support ring 221 and support wall 222 in at least some examples disclosed herein may be constructed from a variety of materials. For example, expandable scaffold of support ring 221 and/or support wall 222 may be constructed from a metal (e.g., Nitinol). In other instances, expandable scaffold of support ring 221 and support wall 222 may be constructed from a polymeric material (e.g., PET). In yet other instances, portions of support member 220 may be constructed from a combination of metallic and polymeric materials. Additionally, support structure 220 or portions thereof may include a bioabsorbable and/or biodegradable material.

In some instances, it may be desirable to design support structure 220 to include a covered portion. For example, support structure 220 may include one or more layers (e.g., covering, coating, etc.) of material positioned on and/or adjacent to the outer and/or inner surface of support structure 220. In some instances, the covering may include an elastomeric or non-elastomeric material. In other instances, the covering may be formed from a suitable material, such as a biostable material. For example, the covering may be a polymeric material, such as silicone, polytetrafluoroethylene, polyurethane, or the like, or other materials including those disclosed herein. Further, the covering may be a biostable material. For purposes of discussion herein, a biostable material may be defined as a material that does not biodegrade.

FIG. 10 further illustrates that stent member 212 may be positioned in a central region of support ring 221 and/or support wall 222. In other words, support ring 221 and/or support wall 222 may extend circumferentially around the outer surface of stent member 212, whereby the shape of support structure 240 may determine the precise positioning of stent member 112 within support ring 221. It is contemplated that stent 212 may be positioned in a variety of positions within support ring 221. Further, similar to the examples described above, support structure 220 may permit stent member 212 to shift longitudinally along the body lumen in which medical device 210 is positioned to accommodate peristaltic motion.

Figure 11:
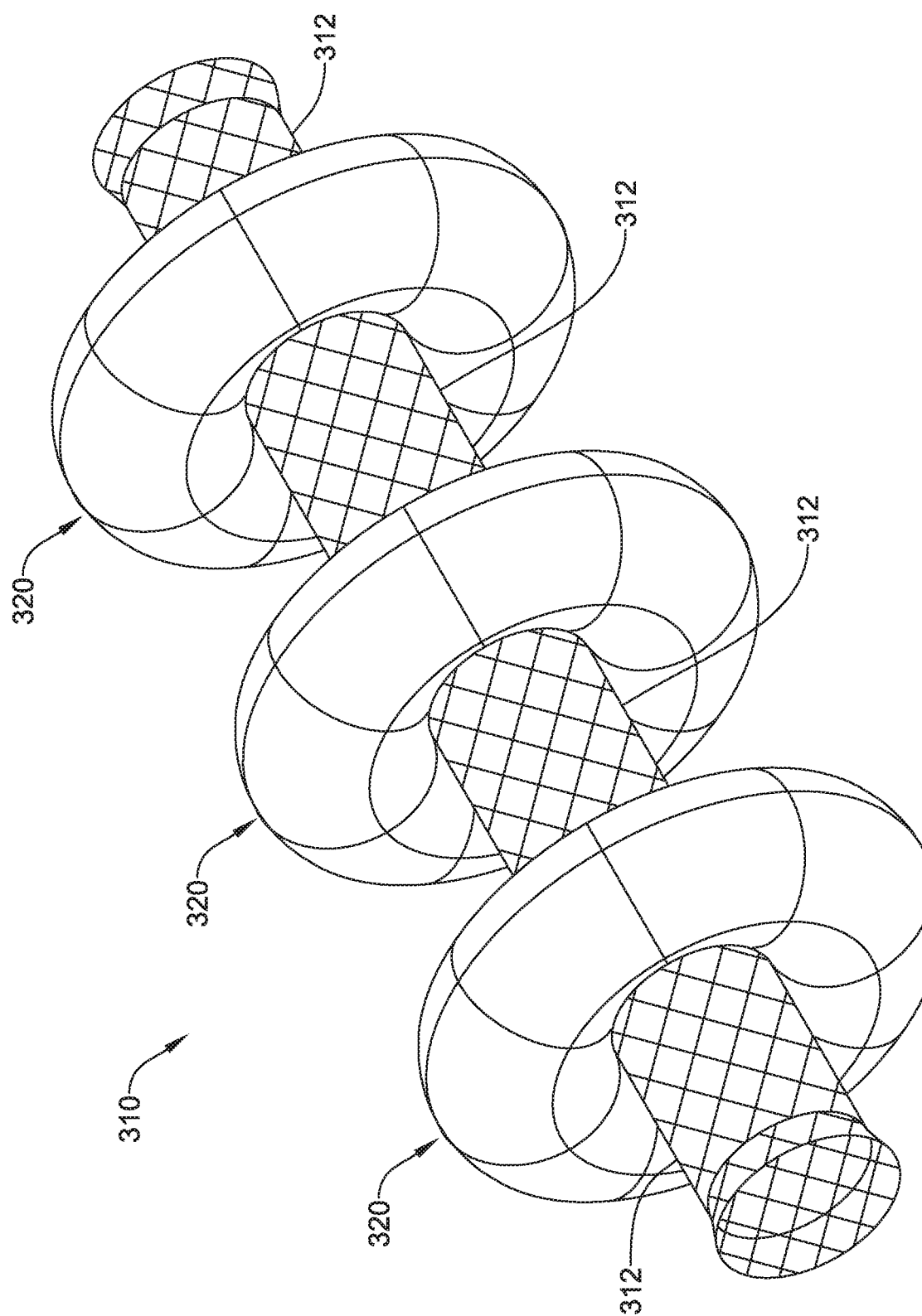
FIG. 11 illustrates another example stent including a support structure; While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

FIG. 11 illustrates another medical device 310. Medical device 310 may be similar in form and function to the medical device (including stent member 12 and supporting member 20) shown in FIG. 1. For example, medical device 310 may include stent 312 and one or more support members 320. FIG. 11 illustrates three separate supporting members 320 arranged along the outer surface of stent 312. However, while medical device 310 shows three separate supporting members 320, it contemplated that medical device 310 may include fewer or greater than three separate supporting members 320. Supporting members 320 may work together to permit stent member 312 to shift longitudinally along the body lumen in which medical device 210 is positioned.

The materials that can be used for the various components of medical device 10 (and/or other stents disclosed herein) and the various tubular members disclosed herein may include those commonly associated with medical devices. For simplicity purposes, the following discussion makes reference to medical device 10 (and/or other medical devices disclosed herein) and other components of medical device 10 (and/or other medical devices disclosed herein). However, this is not intended to limit the devices and methods described herein, as the discussion may be applied to other similar tubular members and/or components of tubular members or devices disclosed herein.

Medical device 10 (and/or other stents disclosed herein) and/or other components of medical device 10 (and/or other medical devices disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of medical device 10 (and/or other medical devices disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of medical device 10 (and/or other medical devices disclosed herein) in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of medical device 10 (and/or other medical devices disclosed herein) to achieve the same result.

In some embodiments, a degree of Magnetic Resonance Imaging (MM) compatibility is imparted into medical device 10 (and/or other medical devices disclosed herein). For example, medical device 10 (and/or other medical devices disclosed herein), or portions thereof, may be made of a material that does not substantially distort the image and create substantial artifacts (e.g., gaps in the image). Certain ferromagnetic materials, for example, may not be suitable because they may create artifacts in an MM image. Medical device 10 (and/or other medical devices disclosed herein), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
    an expandable scaffold positionable within a body lumen, the body lumen having an inner surface, the scaffold including a first end region and a second end region opposite the first end region; and
    a support member extending circumferentially around and attached to an outer surface of the expandable scaffold;
    wherein the support member is configured to be positioned between the outer surface of the expandable scaffold and the inner surface of the body lumen;
    wherein when the scaffold and support member are disposed within the body lumen and the scaffold is in an expanded state, at least a portion of the support member is configured to move axially relative to the inner surface of the body lumen, and wherein moving the support member axially moves the scaffold longitudinally from a first position within the body lumen to a second position within the body lumen with the scaffold in the expanded state to accommodate peristalsis, wherein the first and second end regions of the expandable scaffold extend axially beyond an entirety of the support member in both the first and second positions.

2. The medical device of claim 1, wherein the support member is positioned between the first end region and the second end region.

3. The medical device of claim 2, wherein the first end region, the second end region or both the first and second end regions include a flared portion.

4. The medical device of claim 1, wherein the support member is configured to radially deform.

5. The medical device of claim 1, wherein the expandable scaffold, the support member or both the expandable scaffold and the support member include a covering.

6. The medical device of claim 5, wherein the covering provides a pathway for material to flow therethrough.

7. The medical device of claim 1, wherein the support member comprises a plurality of filaments woven together to form a torus surrounding the expandable scaffold.

8. The medical device of claim 7, wherein the torus includes a centrally located aperture, and wherein the scaffold extends through the centrally located aperture.

9. The medical device of claim 8, wherein the plurality of filaments are woven to the scaffold.

10. The medical device of claim 8, wherein the plurality of filaments are welded to the scaffold.

11. The medical device of claim 8, wherein the torus is configured to roll along the inner surface of the body lumen while remaining attached to the scaffold.

12. The medical device of claim 1, wherein the support member further includes an anchoring member and one or more support arms attached to and extending from the outer surface of the scaffold to the anchoring member.

13. The medical device of claim 12, wherein the plurality of support arms spaced around the outer surface of the expandable scaffold.

14. The medical device of claim 12, wherein the one or more support arms are each attached to the outer surface of the scaffold at an attachment point, and wherein the one or more support arms are configured to pivot about the attachment point as the scaffold moves axially from the first position within the body lumen to the second position within the body lumen.

15. A medical device, comprising:
an expandable stent positionable within a body lumen, the body lumen having an inner surface, the stent including a first end region and a second end region opposite the first end region; and
an expandable support member attached to the stent, the support member including a centrally located aperture;
wherein the stent is configured to extend through the aperture of the support member such that the expandable support member is positioned between the first and second end regions of the stent;
wherein the support member is configured to space the stent away from the inner surface of the body lumen;
wherein when the stent and support member are disposed within the body lumen and the stent is in an expanded state, at least a portion of the support member is configured to move axially relative to the inner surface of the body lumen, and wherein the support member axially moves the stent longitudinally from a first position within the body lumen to a second position within the body lumen with the stent in the expanded state to accommodate peristalsis, wherein the first and second end regions of the expandable stent extend axially beyond an entirety of the support member in both the first and second positions.

16. The medical device of claim 15, wherein first end region, the second end region or both the first and second end regions include a flared portion.

17. The medical device of claim 15, wherein the support member is configured to radially deform.

18. The medical device of claim 15, wherein the stent, the support member or both the stent and the support member include a covering configured to provide a pathway for material to flow therethrough.

19. The medical device of claim 15, wherein the support member comprises a plurality of filaments woven together to form a torus surrounding the stent.

20. A method of treating the esophagus, the method comprising:
advancing a medical device to a target site within the esophagus, the medical device including:
an expandable scaffold having a first end region and a second end region opposite the first end region; and
a support member extending circumferentially around and attached to an outer surface of the expandable scaffold at a position between the first and second end regions of the expandable scaffold;
radially expanding the scaffold and the support member to an expanded state such that the support member is positioned between an inner surface of the esophagus and an outer surface of the stent in the expanded state; and
moving at least a portion of the support member in the expanded state axially relative to the inner surface of the esophagus, wherein moving the support member axially moves the scaffold longitudinally from a first position within the esophagus to a second position to accommodate peristalsis in the esophagus, wherein the first and second end regions of the expandable scaffold extend axially beyond an entirety of the support member in both the first and second positions.

* * * * *